United States Patent [19]

Hinnekens

[11] Patent Number: 4,728,671
[45] Date of Patent: Mar. 1, 1988

[54] PROCESS FOR PRODUCING ALCOHOLS

[75] Inventor: Herve Hinnekens, Sint-Denijs-Westrem, Belgium

[73] Assignee: Oleofina, S.A., Brussels, Belgium

[21] Appl. No.: 727,043

[22] Filed: Apr. 25, 1985

Related U.S. Application Data

[63] Continuation-in-part of Ser. No. 630,038, Jul. 12, 1984, abandoned.

[30] Foreign Application Priority Data

Jul. 14, 1983 [LU] Luxembourg ............................ 84912

[51] Int. Cl.$^4$ .................. C07D 307/44; C07C 29/136; C07C 29/14
[52] U.S. Cl. ..................................... 549/503; 568/799; 568/862; 568/864; 568/881; 568/885; 502/225; 502/244
[58] Field of Search ................ 549/503, 497; 568/799, 568/862, 864, 861, 881, 885; 502/225, 244, 256, 318, 245

[56] References Cited

U.S. PATENT DOCUMENTS 3,886,219  5/1975  Reich ............................. 502/244 X
3,899,446  8/1975  Miya et al. ......................... 502/318
4,302,397  11/1981  Frainier et al. ..................... 549/503

OTHER PUBLICATIONS

Masters, Spray Drying, International Textbook Co. Ltd., London, Eng. (1972), pp. 471–472, 538–540.

Primary Examiner—Joseph L. Schofer
Assistant Examiner—F. M. Teskin
Attorney, Agent, or Firm—John K. Abokhair; Mark A. Montgomery; M. Norwood Cheairs

[57] ABSTRACT

The present invention relates to a process for producing alcohols comprising hydrogenating compounds selected from the group consisting of acids, esters and aldehydes under sufficient hydrogen pressure and temperature in the presence of a catalyst comprising a copper chromite first component and a second component consisting essentially of copper deposited on a support.

23 Claims, No Drawings

PROCESS FOR PRODUCING ALCOHOLS

RELATED APPLICATIONS

This application is a continuation-in-part of copending application Ser. No. 630,038 filed on July 12, 1984, now abandoned, which is hereby incorporated by reference in its entirety.

FIELD OF THE INVENTION

The present invention relates to an improved process for producing alcohols by the hydrogenation of aldehydes, fatty acids and/or alkyl esters of fatty acids. Additionally, the present invention relates to an improved process for producing furfuryl alcohol.

BACKGROUND OF THE INVENTION

The production of fatty alcohols and of furfuryl alcohol is of great interest since these compounds have many applications respectively in the detergent field and for the production of furan resins.

Conventional processes presently used for hydrogenating aldehyde, acid or ester functions, thereby producing an alcohol function, involve very high pressure and very high temperature and therefore require costly and energy-consuming apparatus. In the conventional processes for preparing fatty alcohols by hydrogenation of the corresponding fatty acids or their alkyl esters, the reaction is carried out at a pressure between 250 and 330 bar and a temperature range between 300° and 320° C. When furfuryl alcohol is similarly prepared, the required pressure is usually between 60 and 150 bar.

Furthermore, in conventional processes, the purity of the products obtained, whether fatty alcohol or furfuryl alcohol, is not sufficient for further use. A further distillation step is thus required, which again increases the energy consumption.

Therefore, there is a need in the art to provide a process for producing fatty alcohols or furfuryl alcohol, according to which the hydrogenation of the compounds with an aldehyde, an acid or an ester function is carried out at much lower pressure.

SUMMARY OF THE INVENTION

An object of the present invention therefore is to provide a process for producing alcohols by hydrogenation of corresponding compounds, selected from the group consisting of aldehydes, acids and alkyl esters of these acids, under a relatively low hydrogen pressure and at lower temperatures than those used in conventional processes.

A further object of the present invention is to provide a process for producing fatty alcohols by low-pressure hydrogenation of the corresponding acid, ester or aldehyde.

Still a further object of the present invention is to provide a process whereby the purity of the products obtained is such that no further distillation step is required.

Another object of the present invention is to provide a catalyst for the hydrogenation of aldehydes, particularly furfural, fatty acids and alkyl esters of fatty acids at relatively low pressures.

The process of the present invention for producing alcohols by hydrogenation of compounds with corresponding numbers of carbon atoms, selected from the group consisting of aldehydes, fatty acids and alkyl esters of fatty acids, is characterized in that the hydrogenation is carried out under a hydrogen pressure ranging from about 20 to about 100 bar, at a temperature ranging from about 150° to about 300° C. and in the presence of a catalyst mixture comprising a copper chromite first component, and a second component of copper deposited on a support.

The process of the present invention applies in particular to the production of fatty alcohols with 6 to 24 carbon atoms, by hydrogenation of the corresponding fatty acids or alkyl esters under a hydrogen pressure ranging from about 25 to about 100 bar, at a temperature ranging from about 200° to about 300° C. and in the presence of a catalyst mixture comprising a copper chromite first component and a second component of copper deposited on a support.

The process of the present invention further applies to the production of furfuryl alcohol by hydrogenation of furfural under a hydrogen pressure ranging from about 20 to about 35 bar, at a temperature ranging from about 150° to about 250° C. and in the presence of a catalyst consisting of a copper chromite component on the one hand, and of copper deposited on a support on the other hand.

It has unexpectedly been found that hydrogenation in the presence of the catalyst of the present invention is carried out at pressures and temperatures much lower than those used in the prior art.

DETAILED DESCRIPTION OF PREFERRED EMBODIMENTS

It has been found that fatty alcohols with 6 to 24 carbon atoms, most often with 12 to 18 carbon atoms, may be prepared by hydrogenation of the corresponding fatty acids or alkyl esters, wherein the aliphatic chain of the acid may be branched, under a hydrogen pressure ranging from about 20 to about 80 bar, i.e., under pressures much lower than required by conventional processes, if the hydrogenation reaction takes place in the presence of a catalyst mixture comprising a copper chromite first component prepared in a reducing medium, preferably in the presence of a short-chain aldehyde which in our case is formaldehyde, and a second component of copper deposited by atomization on a support.

In the first component of the catalyst of the present invention, i.e., the copper chromite, the copper amount generally comprises from about 20 to about 40 weight percent (wt. %) of the total amount of copper and chromium calculated as oxides, and preferably from about 30 to about 40 wt. %. Copper chromite catalysts are well known in the art. For example, these catalysts are described in Catalytic Processes and Proven Catalysts, C. L. Thomas, Academic Press 1970, pp. 154–156; Kirk-Othmer ENCYCLOPEDIA OF CHEMICAL TECHNOLOGY, second edition, Vol. 5, p. 496; and Noveau Traite de Chimie Minerale, edited by Masson et al, Libraires de l'Academie de Medecine, 1959, pp. 187–188, which are all hereby incorporated by reference in their entirety.

In general, "copper chromite" really describes or covers a variety of catalyst compositions, all of which contain copper and chromium normally in the form of copper oxide (CuO) and chromium oxide ($Cr_2O_3$). One known method for the preparation of copper chromite is described in U.S. Pat. No. 4,302,397 to Frainier et al, which is hereby incorporated by reference in its entirety, and basically involves the thermal decomposition of the ammonium complex Cu(OH)NH$_4$CrO$_4$ to give the copper chromite Cr$_2$O$_3$.2CuO. Other suitable copper chromite catalysts include those listed in the above-mentioned references and others apparent to one skilled in the art.

The second component of the catalyst is prepared by utilizing atomization to deposit a copper salt, wherein copper has a valency of 2, on a support material. Atomization is well known in the art; see Kirk-Othmer, ENCYCLOPEDIA OF CHEMICAL TECHNOLOGY, second edition, Vol. 18, pp. 634–636, which are hereby incorporated by reference. In general, an aqueous solution of a copper salt is prepared. Suitable copper salts include the chlorides, nitrates, sulfates, carboxylates, acetates, formiates and the like. Generally, copper acetate is utilized. Thereafter, the support material, for example sodium silicate, is introduced into the solution to form a slurry which is subjected to spray drying, i.e., atomization, to form dry particles of support material containing the copper salt therein.

In the second component of the catalyst, copper comprises from about 6 to about 45 weight % of the catalyst, and preferably from about 20 to about 40 weight %. The copper is deposited by atomization on a support which generally has hydroxyl groups on its surface. Suitable supports for the process of the present invention are generally alkaline silicates or aluminates, preferably sodium or potassium silicates or aluminates.

It has been found that in order to hydrogenate fatty acids or alkyl esters of these acids with 6 to 24 carbon atoms, the weight ratio of the components of the catalyst, i.e., copper chromite:Cu-support, should be from about 1:1.5 to about 1:0.75.

When alkyl esters of fatty acids are used, the alkyl radical of these esters may contain between 1 and 25 carbon atoms. However, due to easier supply, methyl esters are preferred.

When a batch process is used, the amount of catalyst to be used during the hydrogenation generally ranges from 0.1 to 5 weight % based on the feed, and preferably from 0.2 to 1 weight %.

It has also been found that furfuryl alcohol may also be prepared in accordance with the present invention by hydrogenation of furfural under a hydrogen pressure ranging from about 20 to about 35 bar, preferably from about 20 and about 30 bar, i.e., under pressures much lower than used in conventional processes.

When a batch process is used, the amount of catalyst to be used for the hydrogenation of furfural also ranges from about 0.1 and about 5 weight % based on the feed, and preferably from about 0.2 to about 1 weight %.

However, it has been found, particularly as far as the hydrogenation of furfural is concerned, that the weight ratio of the components of the catalyst, i.e., copper chromite:Cu-support, preferably had to be from about 1:0.2 to about 1:0.4.

The process of the present invention using said catalyst gives truly unexpected results, as it is well known in the art that, when used alone to hydrogenate the same products, the components of said catalyst never allowed such a reduction of the hydrogen pressure.

While not wishing to be bound in detail by any theory, it may be supposed that the activity of the catalyst used in the process of the invention is stabilized because of the use of a reducing medium during the preparation of the copper chromite mixture and because of the atomization of the copper on the support.

It has also been found that the process of the invention allows operation at lower temperature, generally from about 170° to about 250° C. Further, the products obtained with the process of the invention are of a purity (90 to 99.5% purity) such that no additional distillation is needed.

The process of the invention may be carried out either in batch or continuously. The liquid hourly space velocity (LHSV) in the continuous process is generally from about 0.1 to about 5.

The present invention is also described by the following examples which are meant to be illustrative and are not intended to define the scope of the invention.

EXAMPLE 1

Commercial-grade furfural was catalytically hydrogenated into furfuryl alcohol. The first component of the catalyst, i.e., the copper chromite component, was prepared from a mixture of copper and chromium in a reducing medium, formaldehyde in the present case, the copper amount in said first component being about 40% by weight, expressed as oxide. The other component of the catalyst was copper salt atomized on a sodium silicate support, with copper amounting to 40 weight % of the component. The two components of the catalyst were homogeneously mixed in a copper chromite:Cu-support weight ratio of 1:0.2.

Hydrogenation was carried out under a hydrogen pressure of 25 bar, at a temperature of 180° C. during 45 minutes, and in the presence of an amount of catalyst of 0.25 weight % of the furfural.

Furfuryl alcohol was obtained with a yield of 99.5% and in such a state of purity that no additional distillation was necessary to remove impurities. The composition of the obtained product is indicated in the following Table 1.

TABLE 1

| furfuryl alcohol | 99.8% |
|---|---|
| furfural | traces |
| ash | 0.01% |
| water | 0.1% |

The color according to the Lovibond 5¼ scale is maximum 0.1 red and 0.7 yellow.

By way of comparison, furfural was hydrogenated in the presence of a conventional copper chromite catalyst containing 40 weight % of copper. In order to obtain the same results, it was necessary to operate under a hydrogen pressure of 180 bar.

EXAMPLE 2

Lauryl alcohol was prepared by catalytic hydrogenation of methyl laurate. The first component of the catalyst was prepared from a mixture of copper and chromium in a reducing medium, formaldehyde in the present case, the copper amount in said component being about 35% by weight, expressed as oxide. The other component of the catalyst was copper salt atomized on a sodium silicate support, with copper amounting to 40 weight % of the component. The two components of the catalyst were homogenously mixed in a copper chromite:Cu-support weight ratio of 1:1.5.

Hydrogenation was carried out under a hydrogen pressure of 60 bar, at a temperature of 218° C., and with a flow rate of 22 g methyl laurate per hour on 130 g catalyst, corresponding to a LHSV of 0.24.

Lauryl alcohol was obtained with a very good yield. The product obtained has the following composition:

| | |
|---|---|
| lauryl alcohol | 97.5 weight % |
| methyl laurate | 0.1 weight % |
| lauryl laurate | 2.4 weight % |

EXAMPLE 3

A mixture of cetyl and stearyl alcohols was prepared by catalytic hydrogenation of methyl palmitostearate (50 wt % $C_{16}$ and 50 wt % $C_{18}$). The first component of the catalyst was prepared from a mixture of copper and chromium in a reducing medium, formaldehyde in the present case, the amount of copper in said mixture being about 35% by weight expressed as oxide. The other component of the catalyst was copper atomized on a sodium silicate support, with copper amounting to 40 weight % of the component. The two components of the catalyst were homogeneously mixed in a copper chromite:Cu-support weight ratio of 1:1.

Hydrogenation was carried out under a hydrogen pressure of 65 bar, at a temperature of 218° C. and with a flow rate of 35 g ester per hour on 120 g catalyst, corresponding to a LHSV of 0.4.

The mixture of cetyl and stearyl alcohols was obtained with a very good yield. The product obtained had the following composition:

| | |
|---|---|
| cetyl and stearyl alcohols | 97.5 wt % |
| methyl palmitate and stearate | 0.1 wt % |
| mixture of cetyl and stearyl esters of palmitic and stearic acids | 2.4 wt % |

COMPARATIVE EXAMPLE

The conditions of Example 1 were repeated except that the second component was changed. This second component was prepared by the atomization of copper oxide, CuO, on a sodium silicate support. The furfuryl alcohol yield was only 72.3% which is significantly lower than that of Example 1.

What I claim is:

1. A process for producing alcohols comprising hydrogenating compounds selected from the group consisting of acids, esters and aldehydes under sufficient hydrogen pressure and temperature in the presence of a catalyst comprising a copper/chromite first component prepared in a reducing medium and a second component consisting essentially of copper salt deposited by atomization on a support having surface hydroxyl groups.

2. The process of claim 1 wherein the hydrogen pressure is from about 20 to about 100 bar and the temperature is from about 150° to about 300° C.

3. The process of claim 1 wherein the alcohols produced are fatty alcohols having from 6 to 24 carbon atoms and wherein the hydrogen pressure is from about 25 to about 100 bars and the temperature is from about 150° to about 300° C. and wherein the first component/second component weight ratio is from about 1:1.5 to about 1:0.75.

4. The process of claim 3 wherein the hydrogen pressure is from about 30 to about 80 bar.

5. The process of claim 3 wherein fatty acid alkyl esters are hydrogenated to produce fatty alcohols wherein the alkyl radical of said fatty acid alkyl esters comprises from 1 to 25 carbon atoms.

6. The process of claim 5 wherein the alkyl radical is methyl.

7. The process of claim 1 wherein the catalyst first component comprises from about 20 to about 40% by weight copper expressed as oxide and based on the total weight of copper and chromium as oxides, and wherein the second component comprises from about 5 to about 45% by weight copper based on the total weight of the copper and the support.

8. The process of claim 7 wherein the catalyst first component comprises copper in an amount from about 30 to about 40% by weight.

9. The process of claim 7 wherein the catalyst second component comprises copper in an amount from about 20 to about 40% by weight.

10. The process of claim 1 wherein the reducing medium is formaldehyde.

11. The process of claim 1 wherein the support is selected from the group consisting of alkali metal silicates, alkali metal aluminates or any combination thereof.

12. The process of claim 1 wherein the weight ratio of the catalyst first component to the catalyst second component is from about 1:1.5 to about 1:0.75.

13. The process of claim 1 carried out batchwise wherein the catalyst is present in an amount of from about 0.1 to about 5% by weight based on the weight of reactants.

14. The process of claim 13 wherein the catalyst is present in an amount of from about 0.2 to about 1.0% by weight.

15. The process of claim 1 carried out continuously at a liquid hourly space velocity of from about 0.1 to about 5.0.

16. The process of claim 1 wherein the alcohols produced are at least 90% pure.

17. A process for producing furfuryl alcohols by hydrogenation of furfuryl aldehyde under sufficient hydrogen pressure and temperature in the presence of a catalyst comprising a copper chromite first component prepared in a reducing medium and a second component consisting essentially of copper salt deposited by atomization on a support material having surface hydroxyl groups.

18. The process of claim 17 wherein the hydrogen pressure is from about 20 to about 35 bar and the temperature is from about 150° to about 250° C.

19. The process of claim 17 wherein the catalyst first component comprises from about 20 to about 40% by weight copper expressed as oxide and based on the total weight of copper and chromium as oxides, and wherein the second component comprises from about 5 to about 45% by weight copper based on the total weight of the copper and the support.

20. The process of claim 17 wherein the reducing medium is formaldehyde.

21. The process of claim 17 wherein the catalyst first component and second component are present in a weight ratio of from about 1:0.2 to about 1:0.4.

22. The process of claim 17 wherein the furfuryl alcohol produced is at least 95 percent pure.

23. A process for producing alcohols comprising hydrogenating compounds selected from the group consisting of acids, esters, and aldehydes under sufficient hydrogen pressure and temperature in the presence of a catalyst comprising:
   (a) a copper chromite first component prepared in a reducing medium; and
   (b) a second component prepared by depositing a copper salt on a support material by atomization wherein the support material comprises surface hydroxyl groups.

* * * * *